United States Patent [19]

Lutenegger et al.

[11] Patent Number: 4,458,525
[45] Date of Patent: Jul. 10, 1984

[54] BOREHOLE PLATE TEST

[75] Inventors: Alan J. Lutenegger; Richard L. Handy, both of Ames, Iowa

[73] Assignee: Iowa State University Research Foundation, Inc., Ames, Iowa

[21] Appl. No.: 366,543

[22] Filed: Apr. 8, 1982

[51] Int. Cl.³ .............................................. G01N 3/00
[52] U.S. Cl. ..................................................... 73/84
[58] Field of Search .................... 73/84, 784, 822, 151

[56] References Cited

U.S. PATENT DOCUMENTS 3,481,188 12/1969 Mori ........................................ 73/84
4,353,247 10/1982 DeDomenico ......................... 73/84

FOREIGN PATENT DOCUMENTS 286480 3/1928 United Kingdom .................... 73/84

Primary Examiner—Anthony V. Ciarlante
Attorney, Agent, or Firm—Zarley, McKee, Thomte, Voorhees & Sease

[57] ABSTRACT

A method of insitu testing of soil compressibility comprises boring a hole in the soil to be tested, reconstituting the lateral stress environment in the soil adjacent the bottom of the borehole and then performing vertical compression tests directly on the undisturbed material at the bottom of the borehole. The testing apparatus of the invention includes a cylindrical container adapted to be pushed to the bottom of the borehole. An inflatable circumferential membrane around the exterior periphery of the container is inflated to reconstitute the lateral stress environment. The load may be applied to the base of the borehole by either a closed or inflatable fluid cell or directly by a flat or stepped load plate.

In one embodiment of the invention, a thin-walled cylindrical tube penetrates the soil at the base of the borehole so as to laterally support the test soil for substantially one-dimensional vertical compression testing.

24 Claims, 6 Drawing Figures

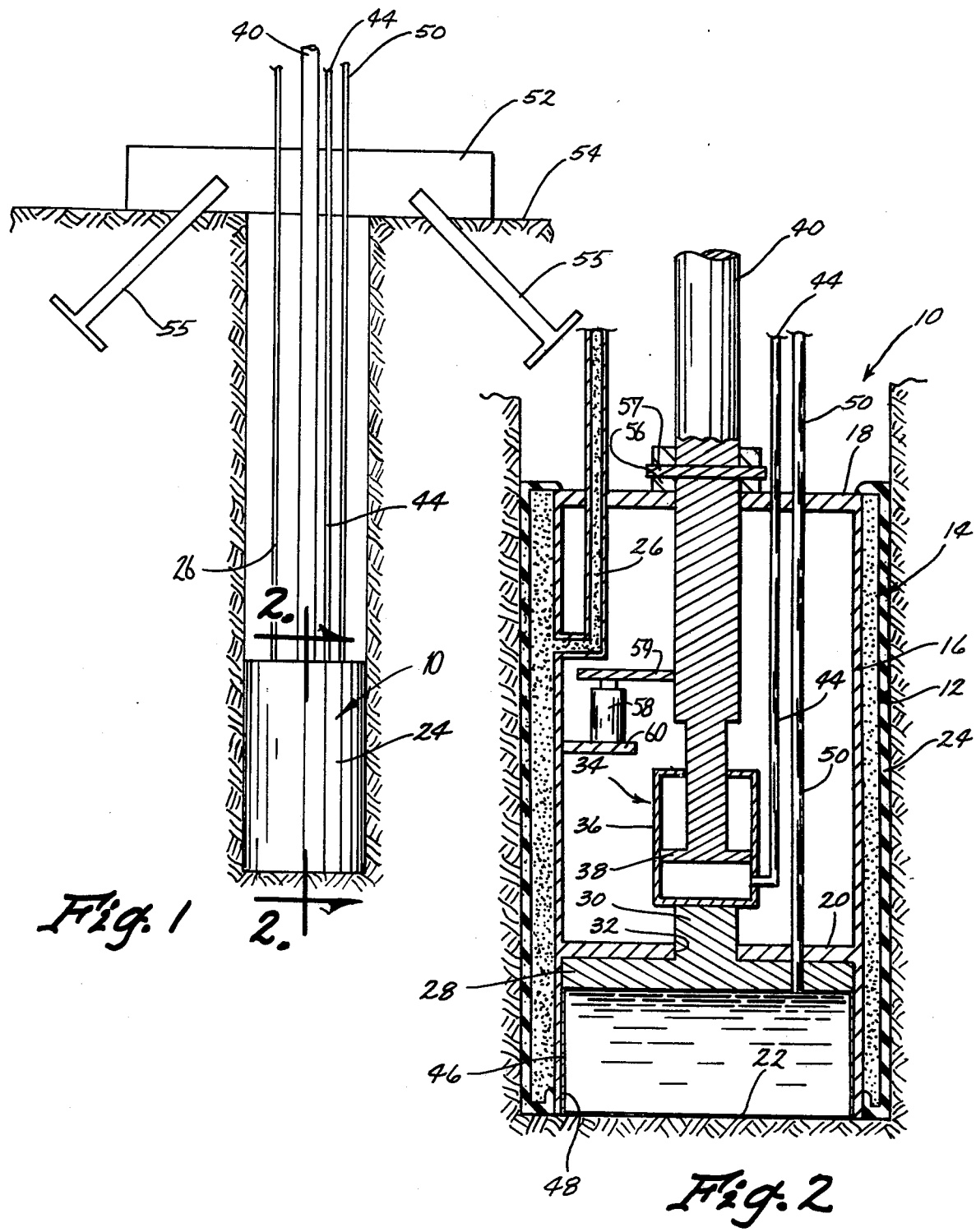

BOREHOLE PLATE TEST

BACKGROUND OF THE INVENTION

The present invention relates to the measurement of soil compressibility and more particularly to an improved method and apparatus of insitu soil testing for determining soil compressibility at the base of a borehole.

The testing of soil compressibility at a construction site is important for determining the type of foundation which must be built to support a given building. Current methods available for determining the insitu characteristics of soil compressibility are basically of two types, plate bearing and pressuremeter.

In the plate bearing method, a plate is situated on the smoothed surface of the ground and its deflection is measured under incrementally increasing load. An acknowledged serious limitation of this test is that only near-surface soil contributes to settlement whereas the depth of influence of an actual foundation may be many times deeper. Therefore, if the soil changes with depth, the plate load test is not usable, or a pit must be prepared at great expense to conduct the test deep below the existing ground elevation.

The pressuremeters basically consist of a multi-chamber inflatable bag wherein lateral soil compressibility is monitored from a measured pressure versus volume relationship. The limitation of the pressuremeters is that only the lateral compressibility, not the vertical compressibility, is measured whereas placed on the soil or rock.

To overcome these limitations, two different types of tests have been proposed. The first is to conduct a type of plate test in the base of a borehole and the second involves laboratory testing of so-called "undisturbed" soil samples. But in each instance, the disturbance of the stress environment in the soil at the test site is reflected in the test results making them somewhat less than reliable.

Accordingly, a primary object of the present invention is to provide an improved method and apparatus of insitu soil testing for determining soil compressibility.

Another object is an insitu soil testing method and apparatus which produces a direct measure of soil compressibility in a vertical direction.

Another object is an insitu soil testing method and apparatus wherein tests may be conveniently conducted at the base of a borehole.

A related object is an insitu soil testing method and apparatus wherein tests may be conducted at any desired depth.

Another object is an insitu soil testing method and apparatus wherein the natural lateral stress environment of the soil at the base of a borehole is reconstituted prior to testing.

A specific object is an insitu soil testing method and apparatus wherein the test soil is laterally stabilized for substantially one-dimensional vertical compression testing.

Another object is an insitu soil testing method and apparatus providing for drainage of the test soil to enable measurement of the drained load deformation characteristics.

Finally, an object is an insitu soil testing method and apparatus which are simple, economical and efficient.

SUMMARY OF THE INVENTION

The insitu soil testing method of the present invention includes the steps of boring a hole in the soil to be tested, reconstituting the lateral stress environment in the soil adjacent the bottom of the borehole and then performing a vertical compression test directly on the undisturbed material at the base of the borehole. The apparatus for performing the method of the invention may comprise a cylindrical container adapted to be lowered to the bottom of a borehole prior to testing. The container has an inflatable circumferential membrane around the exterior periphery thereof which is inflated to reconstitute the lateral stress environment. An open bottomed compartment at the lower end of the container has an axially slidable load plate therein from which an elongated load rod extends axially up through the borehole to the surface. A fluid cell may be interposed between the load plate and soil at the base of the borehole. For a closed cell, the load may be applied either from the surface with dead load or a screw mechanism, or in the hole with a fluid cylinder unit. For an inflatable cell, the load rod need only be anchored whereupon the load is applied directly upon inflation.

Further alternatives to the basic method further include the use of a flat end plate directly without a fluid cell or a multi-stepped load plate for correcting problems of perimeter shear.

For measurement of substantially one-dimensional vertical compression, a thin-walled cylindrical housing is pushed into the soil at the bottom of a borehole to laterally stabilize the soil prior to vertical loading.

BRIEF DESCRIPTION OF THE DRAWINGS

FIG. 1 is a partially sectional side view of the soil testing apparatus installed in a borehole.

FIG. 2 is an enlarged detail sectional view as seen on line 2—2 in FIG. 1;

DESCRIPTION OF THE PREFERRED EMBODIMENTS

Figure 3:
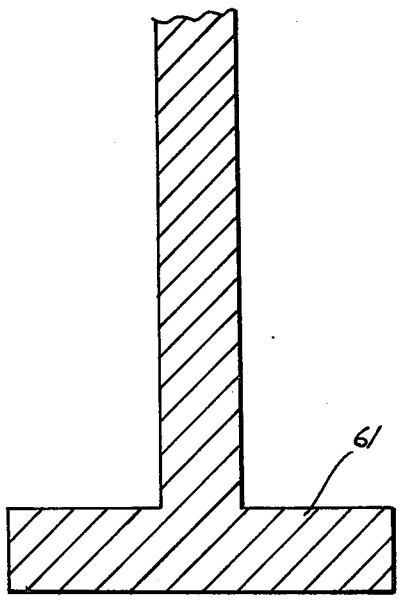
FIG. 3 is a foreshortened side view of an optional flat load plate.

An apparatus 10 for insitu testing of soil compressibility is shown in FIGS. 1 and 2 installed within a borehole 12 which is formed in the soil to be tested.

A generally cylindrical container 14 having a continuous sidewall 16, top wall 18 and medial wall 20 is pushed to the bottom of borehole 12 to the extent of engagement with the bottom 22 of the borehole.

The boring of hole 12 tends to relieve the lateral stress in the soil adjacent the hole. To compensate for this, container 14 has an inflatable circumferential membrane 24 around the exterior periphery of sidewall 16. A fluid conduit 26 extends from the membrane into the container through sidewall 16 and upwardly through top wall 18 for communication with a fluid source. By pumping fluid through conduit 26, membrane 24 may be inflated to a volume and pressure corresponding to the insitu lateral stress environment of the soil prior to boring.

A circular load plate 28 is slidably movable within container 14 below medial wall 20 with its stem 30 extending upwardly through a central opening 32 in wall 20.

A fluid cylinder unit 34 includes a cylindrical housing 36 which bears against the stem 30 for applying a vertical load thereto. The piston 38 within housing 36 is formed as the lower end of an elongated rod 40 which extends upwardly through top wall 18 to the surface for use in applying a load to the soil as explained hereinbelow. A fluid conduit 44 extends from the bottom cylindrical housing 36 to the surface for supplying fluid to the fluid cylinder unit 34 or monitoring the pressure therein.

A fluid cell or load cell 46 is positioned below load plate 28 within the open-bottomed compartment 48 at the bottom of container 14. Whereas fluid cell 46 is shown as an inflatable cell having a fluid conduit 50 extending upwardly through load plate 28 and walls 20 and 18, a closed fluid reservoir could also be utilized as explained hereinbelow.

In operation, after borehole 12 is formed and container 14 is pushed to the bottom 22 of the borehole, fluid is pumped into the circumferential membrane 24 through conduit 26. The fluid pressure within the membrane 24 is simultaneously monitored to cut off fluid flow when the insitu lateral stress is achieved. Insitu lateral stress may be calculated by multiplying the product of the depth of testing and soil unit weight by the coefficient of earth pressure at rest. This coefficient may be estimated by empirical means or the lateral stress may be measured by self-boring pressuremeters.

Compressibility tests are then performed by applying a load to the bottom 22 of borehole 12 and measuring the vertical deflection of the soil. There are several possible ways of applying a load. One method is simply to direct fluid downwardly through conduit 50 for inflating fluid cell 46. Measurements of both the volume and pressure of fluid within the cell are determinative of both the vertical load and resultant soil deformation.

To securely fix the container 14 within the borehole for this test, the upper end of rod 40 is secured to a reaction beam 52 as shown in FIG. 1. Beam 52 is securely anchored to the ground surface 54 by a plurality of helical screw anchors indicated at 55.

To fix the lower end of axial rod 40 relative to container 14, a collar 56 is secured to top wall 18 and a pin 57 is insertable through registered bores through the collar 56 and rod 40. Thus, the reaction from load applied to the lower membrane 22 (or the load plates shown in FIGS. 3-5) can be taken up by the pressure applied by the circumferential membrane 24. Vertical movement is then measured by a linear variable differential transducer 58 installed inside container 14 between brackets 59 and 60 on the rod 40 and side wall 16 respectively. This arrangement eliminates bending which could take place in rod 40 in deep holes. Rod 40 is then merely a placement rod. The cylindrical container 14 will thus have to be long enough so that sufficient reaction is provided to allow testing to the desired vertical load range.

In another method of applying a load to the bottom 22 of borehole 12, the fluid conduit 50 to fluid cell 46 is closed, whereupon the volume of the fluid cell 46 is fixed due to the incompressible character of the fluid therein. Hydraulic oil is a typical fluid suitable for load cell 46. Downward pressure is applied to the load plate 28 by directing fluid into fluid cylinder unit 34 through conduit 44. Rod 40 is again anchored as in the previous test. The pressure within fluid cylinder unit 34 and fluid cell 46 are indicative of the vertical load and the volume of flow to the fluid cylinder unit is indicative of the vertical deformation of the soil.

Finally, as a further alternative, both fluid conduits 44 and 50 may be closed and pin 57 may be removed from collar 56, whereupon a downward vertical force may be applied directly through rod 40 from the surface with a dead load such as weight or a screw mechanism, not shown. In this instance, the actual weight or the pressure within fluid cell 46 are indicative of the load and the axial movement of rod 40 corresponds to the vertical soil deformation.

Figure 4:
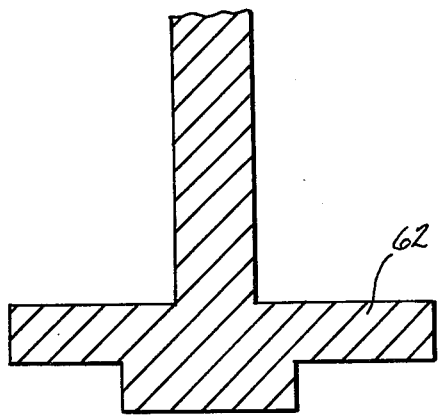
FIG. 4 is a foreshortened side view of an optional two-stepped load plate.

Referring to FIG. 3, an optional flat load plate 61 may be substituted for the load plate 28 and fluid cell 46. The advantage of a flat end plate is to simulate a rigid foundation. An alternative to end plate 61 is to use a different sized end plate such as a multi-stepped plunger or end plate 62 as shown in FIG. 4, to provide multiplicity of results.

Figure 5:
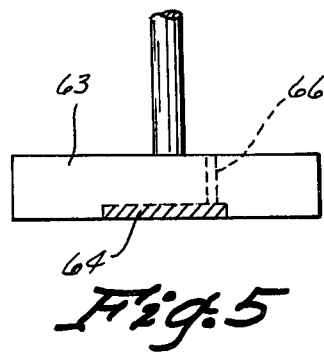
FIG. 5 is a foreshortened side view of an optional flat load plate including a drainage passage therethrough.

A further alternative load plate 63 is shown in FIG. 5 with a disc 64 of porous stone, brass or the like countersunk into the bottom surface so as to be flush. An exhaust opening 66 opens through the top of load plate 63 to provide drainage through the load plate to measure the drained characteristics of load-deformation or to provide means to measure pore water pressure, such as with electrical transducers.

Load-unload cycles may be easily performed by monitoring the deformation and rebound during repeated cyclic loading. Such information may be pertinent to aid in defining the influence of sampling or excavation procedures.

Use of either a dead-load procedure or the fluid cylinder unit 34 will supply a constant load to the load plate. For saturated soils, by taking deformation readings at timed intervals from the initiation of each load, the coefficient of consolidation, or time rate of deformation may be determined. In the case of unsaturated soils, the creep rate is determined.

Figure 6:
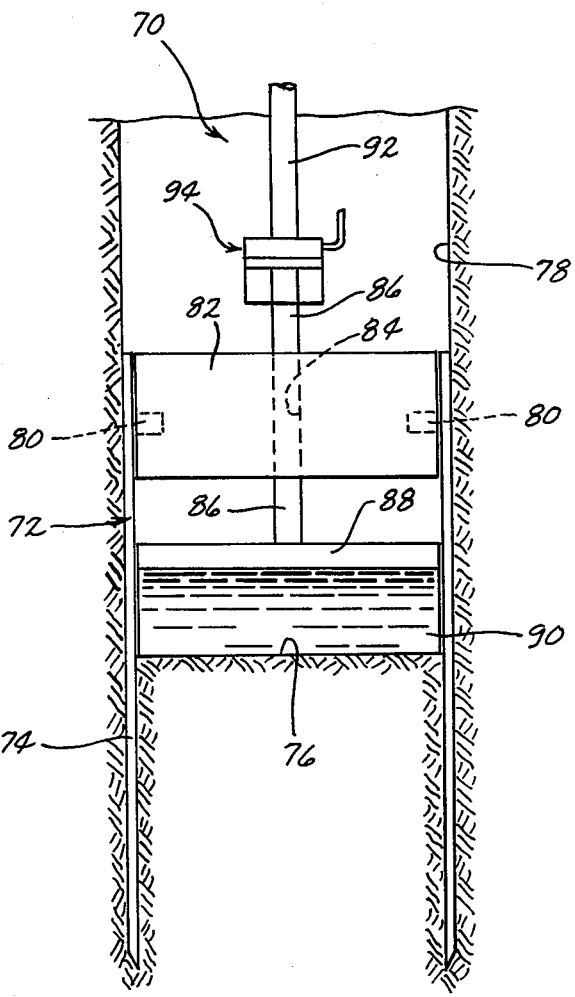
FIG. 6 is a side view of an alternate shielding structure for the load plate.

The apparatus described above and shown in FIGS. 1 and 2 provides loading such that deformations in the soil at the point of loading occur in three-dimensional space. This is usually desirable, since most realistic conditions would have this characteristic. In the special case where only one-dimensional compression is possible, an alternative test may be performed with the apparatus 70 shown in FIG. 6. The apparatus 70 includes an elongated thin-walled cylindrical housing 72 having a lower end 74 adapted for penetration into the soil below the bottom 76 of bore 78. Housing 72 may be a standard Shelby thin-walled tube attached with set screws 80 to an annular top wall 82 having a central bore 84 for slidably receiving the stem 86 of load plate 88. The load plate may be used in conjunction with a fluid cell 90 and the vertical load may be applied either directly through the corresponding load rod 92 or through the fluid cylinder unit 94 interposed between load rod 92 and load plate stem 86. Once the housing 72 is in place, the load may be directly applied since the lateral stress of the soil within the lower end 74 of the cylindrical housing 72 has not been relieved.

Whereas the preferred methods and apparatus for insitu testing of soil compressibility has been shown and described herein, many modifications, alterations and substitutions may be made which are within the intended broad scope of the appended claims. For example, the hole may be bored to incremental depths with tests conducted at each step thereby allowing layered systems to be analyzed individually so that a more precise estimate of settlement may be made.

Thus there has been shown and described a method and apparatus for insitu testing of soil compressibility which accomplishes at least all of the stated objects.

We claim:

1. A method of insitu soil testing for determining soil compressibility, comprising,
   boring a hole in the soil to be tested,
   reconstituting the lateral stress environment in the soil adjacent the bottom of the borehole,
   said reconstituting of lateral stress environment being accomplished by lowering a cylindrical housing having an inflatable circumferential membrane thereon into said borehole into engagement with the soil at the bottom thereof, and inflating said membrane to a predetermined volume and pressure which corresponds to the insitu lateral stress environment of the soil prior to boring;
   applying a load to the soil at the bottom of the borehole, and
   measuring the compression of said soil in response to the application of said load.

2. The method of claim 1 wherein the step of applying a load includes providing a load plate axially slidably mounted within said housing and exerting a downward force on said load plate.

3. The method of claim 2 further comprising interposing a fluid cell between said load plate and soil.

4. The method of claim 2 wherein the step of exerting a downward force is accomplished by a fluid cylinder mounted within said housing.

5. A method of claim 3 further comprising providing fluid drainage through said load plate while exerting a downward force thereon by means of a drainage means extending through said load plate.

6. The method of claim 1 wherein applying a load comprises providing a multi-stepped plunger, placing said plunger in engagement with the soil at the bottom of the borehole and exerting a downward force on said plunger.

7. The method of claim 1 further comprising applying a constant load to the plate, and taking deformation readings at timed intervals from the initiation of said load.

8. The method of claim 1 further comprising producing a plot of applied load versus deformation.

9. A method of claim 1 further comprising applying said load in repeated cycles and monitoring the deformation and rebound responses of said soil during said repeated cyclic loading.

10. A method of insitu soil testing for determining substantially one-dimensional vertical compression, comprising,
    boring a hole in the soil to be tested,
    providing a thin-walled cylindrical housing,
    pushing said thin-walled housing into the soil at the bottom of the borehole,
    applying a vertical load to the soil within said housing at the bottom of the borehole, and
    measuring the compression of said soil responsive to said load.

11. The method of claim 10 wherein said thin-walled housing has an outer diameter substantially equal to the diameter of said borehole.

12. The method of claim 10 wherein the step of applying a vertical load includes providing a load plate axially slidably mounted within said housing and having a stem portion extended upwardly therefrom, and exerting a downward force on said stem.

13. The method of claim 12 further comprising interposing a fluid cell between said load plate and soil.

14. An apparatus for insitu testing of soil compressiblity, comprising,
    a generally cylindrical container adapted for insertion into a generally vertical borehole in soil, said container having upper and lower ends and an open bottomed compartment at the lower end thereof,
    an inflatable circumferential membrane around the exterior periphery of said container adjacent said lower end thereof,
    means for inflating said membrane between said container and the wall of a borehole thereby to reconstitute the lateral stress environment in the soil near the bottom of the borehole, and
    means in the open bottomed compartment for applying an axial load against the bottom of a borehole.

15. The apparatus of claim 14 wherein said means for applying an axial load comprises a circular load plate and means for applying a vertical load to said load plate.

16. The apparatus of claim 15 wherein said load plate is spaced from the bottom end of said container and further comprising a load cell substantially filling the volume between said load plate and lower end of said container.

17. The apparatus of claim 16 wherein said load cell includes an elongated fluid conduit having one end in communication with said load cell and an opposite end extended upwardly through a hole provided therefor in said load plate for fluid communication between said load cell and a source of fluid.

18. The apparatus of claim 15 wherein said means for applying a vertical load to said load plate comprises an elongated load rod extended upwardly from said load plate.

19. The apparatus of claim 18 further comprising a fluid cylinder unit interposed between said load rod and load plate.

20. The apparatus of claim 19 wherein said fluid cylinder unit is disposed within said cylindrical container.

21. The apparatus of claim 15 wherein said load plate includes a coaxial reduced diameter downward extension.

22. Apparatus for in situ soil testing comprising: a bore hole formed in the soil to be tested comprising
    cylindrical side walls, an open upper end, and a bottom;
    an elongated cylindrical thin walled housing having cylindrical housing walls, an upper end, and an open lower end, said housing being fitted within said bore hole with said cylindrical housing walls in frictional facing engagement with said cylindrical side walls of said bore hole,
    said cyindrical housing walls having lower edges penetrating within the soil below the bottom of said borehole;
    a top wall secured to said housing adjacent said upper end of said housing and having a central opening therein;
    a circular load plate axially slidable within said housing below said top wall and above said bottom of said bore hole;

stem means connected to said load plate and extending upwardly through said central opening of said top wall; and power means connected to said stem for applying a predetermined downward force to said load plate so as to cause said load plate to apply a predetermined load to said bottom of said bore hole and means for measuring the compression of said sail in response to the application of said load.

23. Apparatus according to claim 22 wherein a fluid cell is positioned between said load plate and said bottom of said bore hole for causing even distribution of the load from said load plate across the area of said bottom of said bore hole.

24. Apparatus according to claim 22 wherein a load rod includes a lower end operatively connected to said stem for exerting a downward force thereon, said power means comprisng a fluid cylinder unit interposed between said stem and said load rod.

* * * * *